(12) United States Patent
Rhodey

(10) Patent No.: US 10,113,123 B2
(45) Date of Patent: Oct. 30, 2018

(54) PROCESS AND SYSTEM FOR EXTRACTION OF A FEEDSTOCK

(71) Applicant: William George Rhodey, Calgary (CA)

(72) Inventor: William George Rhodey, Calgary (CA)

( * ) Notice: Subject to any disclaimer, the term of this patent is extended or adjusted under 35 U.S.C. 154(b) by 0 days.

(21) Appl. No.: 15/436,025

(22) Filed: Feb. 17, 2017

(65) Prior Publication Data

US 2017/0158974 A1    Jun. 8, 2017

Related U.S. Application Data

(63) Continuation of application No. 14/543,117, filed on Nov. 17, 2014, now Pat. No. 9,611,190, which is a continuation of application No. 11/701,931, filed on Feb. 2, 2007, now Pat. No. 8,889,943, which is a continuation of application No. 10/425,650, filed on Apr. 30, 2003, now abandoned.

(51) Int. Cl.
    *C10G 69/08*    (2006.01)
(52) U.S. Cl.
    CPC ......... *C10G 69/08* (2013.01); *C10G 2400/30* (2013.01)
(58) Field of Classification Search
    CPC ........... B01J 2219/00006; C10G 69/08; C10G 2400/30
    See application file for complete search history.

(56) References Cited

U.S. PATENT DOCUMENTS

| | | |
|---|---|---|
| 2,867,576 A | 1/1959 | Honeycutt |
| 2,880,164 A | 3/1959 | Viland |
| 2,891,901 A | 6/1959 | Donaldson |
| 2,932,612 A | 4/1960 | Galstaun et al. |
| 2,944,959 A | 7/1960 | Kline et al. |
| 2,956,005 A | 10/1960 | Lutz et al. |
| 2,965,561 A | 12/1960 | Carr et al. |
| 2,969,317 A | 1/1961 | Hess |
| 2,981,675 A | 4/1961 | Hemminger |
| 3,003,949 A | 10/1961 | Merryfield |
| 3,013,088 A | 12/1961 | Merryfield |
| 3,018,244 A | 1/1962 | Stanford et al. |
| 3,070,637 A | 12/1962 | Honeycutt |
| 3,121,676 A | 2/1964 | Skraba |
| 3,172,841 A | 3/1965 | Paterson |
| 3,409,540 A | 11/1968 | Gould et al. |

(Continued)

FOREIGN PATENT DOCUMENTS

| | | |
|---|---|---|
| CA | 2485465 A1 | 10/2004 |
| WO | WO-2008043066 A2 | 4/2008 |

(Continued)

OTHER PUBLICATIONS

MacLaren D.D., "Catalytic Reforming", "Petroleum Engineering Course", pp. 1-13 (1955).

(Continued)

*Primary Examiner* — Randy Boyer
(74) *Attorney, Agent, or Firm* — Adler Pollock & Sheehan P.C.; Daniel J. Holmander, Esq.

(57) ABSTRACT

The present invention relates to a method and system for recovering aromatics from a naphtha feedstock obtained from a crude petroleum, natural gas condensate, or petrochemical feedstock. The method and system comprise the steps of recovering an aromatics fraction from the feedstock prior to reforming.

14 Claims, 2 Drawing Sheets

(56) References Cited

U.S. PATENT DOCUMENTS

| | | | |
|---|---|---|---|
| 3,420,907 A | | 1/1969 | Cabbage |
| 3,644,196 A | * | 2/1972 | Lawson ............... C07C 13/10 208/57 |
| 3,753,891 A | | 8/1973 | Graven et al. |
| 3,776,949 A | | 12/1973 | Gelbein et al. |
| 4,053,388 A | | 10/1977 | Bailey |
| 4,115,247 A | | 9/1978 | Lehman et al. |
| 4,167,472 A | | 9/1979 | Dick et al. |
| 4,358,364 A | | 11/1982 | Klosek et al. |
| 4,594,145 A | | 6/1986 | Roarty |
| 4,645,586 A | | 2/1987 | Buss |
| 4,839,024 A | | 6/1989 | Ramage et al. |
| 4,897,177 A | | 1/1990 | Nadler |
| 5,685,972 A | | 11/1997 | Timken et al. |
| 6,051,128 A | | 4/2000 | Nacamuli et al. |
| 6,602,404 B2 | | 8/2003 | Walsh et al. |
| 2004/0218547 A1 | | 11/2004 | Rhodey |
| 2007/0129590 A1 | | 6/2007 | Rhodey |

FOREIGN PATENT DOCUMENTS

| | | |
|---|---|---|
| WO | WO-2008045730 A1 | 4/2008 |
| WO | WO-2008082842 A1 | 7/2008 |

OTHER PUBLICATIONS

Morris W., "Calculating High Cetane 300-400° F.-Cut for Diesel", Oil & Gas Journal, pp. 46-48 (Feb. 8, 2010).

Peavy C.C., "The Importance of Platinum in Petroleum Refinng-Catalytic Reforming in Modern Processing Practice", Platinum Metals Rev. 2(2): 48-52 (1958).

Rhodey W.G., Amended Application filed Feb. 14, 2006 in U.S. Appl. No. 10/425,650.

UOP A Honeywell Company: "Cycler™: Aromatics", UOP LLC (2006).

UOP: "Minalk™ Process for Fixed-Bed Naphtha Sweetening"; UOP LLC (2003).

UOP: "CCR Platforming™ Process", UOP LLC (1999).

UOP: "CCR Platforming™ Process for Motor Fuel Production", UOP LLC (2004).

International Preliminary Report on Patentability together with the Written Opinion dated Aug. 13, 2009.

Australian Office Action dated Jul. 27, 2011 received in related Application No. 2007345527.

Canadian Office Action dated Nov. 29, 2013 received in related Application No. 2,674,212.

Canadian Office Action dated Feb. 5, 2013 received in related Application No. 2,674,212.

Abstract of Canadian Patent Application No. 2,512,457, dated Aug. 19, 2004, corresponding to PCT International Application No. PCT/US2003/041473, filed Dec. 30, 2003.

Examination Report dated Nov. 22, 2010 received in related Application No. GB0914144.1.

U.S. Final Office Action dated Oct. 14, 2010 issued in corresponding U.S. Appl. No. 13/701.931.

U.S. Office Action dated Apr. 27, 2010 issued in corresponding U.S. Appl. No. 13/701,931.

U.S. Final Office Action dated Aug. 4, 2006 issued in corresponding U.S. Appl. No. 10/425,650.

U.S. Office Action dated Aug. 18, 2005 issued in corresponding U.S. Appl. No. 10/425,650.

* cited by examiner

PROCESS AND SYSTEM FOR EXTRACTION OF A FEEDSTOCK

CROSS-REFERENCE TO RELATED APPLICATIONS

This application is a continuation of U.S. patent application Ser. No. 14/543,117 filed on Nov. 17, 2014, which claims priority to U.S. application Ser. No. 11/701,931 filed Feb. 2, 2007, which is a continuation of U.S. application Ser. No. 10/425,650 filed Apr. 30, 2003, now abandoned, the contents of which are incorporated herein by reference in their entirety.

FIELD

The present invention relates to a process and system for extraction of chemical components from a feedstock, such as a petroleum, natural gas condensate, or petrochemical feedstock.

BACKGROUND

In a conventional petroleum or petrochemical refinery process and system, crude feedstock is processed by a crude distillation unit. The crude feedstock may comprise crude oil and/or feedstock having undergone partial processing ("intermediate refinery feedstock"). The crude distillation unit produces a naphtha fraction, together with a number of other fractions useful in production of refined oil products, for example, gasoline, jet fuel, diesel, etc., and fractions useful for the production of specialty chemicals.

The naphtha fraction is primarily composed of paraffins, olefins, naphthenes and aromatics. Paraffins are alkane hydrocarbons of general formula $C_nH_{2n+2}$, which may be substituted, and wherein n is a whole number; e.g., from 1-14. The term "paraffins" is also generally understood to include isoparaffins. Olefins are hydrocarbons having at least one carbon-carbon double bond, such as an alkenes of general formula $C_nH_{2n}$, which may be substituted and wherein n is a whole number; e.g., from 2-14. The olefin fraction may also comprise alkynes of general formula $C_nH_{2n-2}$, which may be substituted and wherein n is a whole number; e.g., from 2-14. When n is greater than 12 and less than 21, the fraction may be referred to as distillates; e.g., jet fuel, diesel, etc. Higher n fractions may be useful for other purposes. Olefins (including substituted olefins) where n=12-14 may be found in both the naphtha fraction and the distillates fraction. The naphthenes include cycloalkanes and alkyl substituted cycloalkanes. Many naphthenes are chemical precursors to the aromatics. The aromatics found in a petroleum or petrochemical feedstock include a range of conjugated hydrocarbon rings and alkyl substituted conjugated hydrocarbon rings.

Hydrocarbon fractions are often referred to as $C_n$ fractions or $C_n^+$ fractions with n being a whole number. It is to be understood that $C_n^+$ includes the $n^{th}$ fraction (i.e., the $C_n$ fraction) as well as higher n fractions.

The whole range naphtha fraction from the crude distillation unit is processed in a naphtha splitter producing an overhead stream (typically referred to as a Light Straight Run or LSR), and a bottoms stream of heavy naphtha. The LSR is rich in paraffins, and the heavy naphtha is rich in naphthenes and aromatics. The heavy naphtha bottoms stream is hydrotreated to remove sulphur and other contaminants, obtaining a sweet naphtha, which is fed to a naphtha reformer where it may be combined with other intermediate sweet naphtha streams, for example, sweet natural gas condensates and hydrocracker naphtha. In the naphtha reformer, the naphtha components are reformulated into components of a gasoline product.

The naphtha reformer is usually a high severity reformer, which produces aromatics, including benzene, toluene and xylenes ("BTX"), as well as other aromatics that enable the reformate to have an octane quality sufficient to meet gasoline octane specifications. Benzene, toluene and xylenes may all also be used in the production of petrochemical derivatives. Of the xylenes that may be used in the production of petrochemical derivatives, para- and ortho-xylene are worth particular mention, although meta-xylenes may also be of value.

High severity reformers are run at high temperatures (e.g., inlet temperatures of about 900 degrees Fahrenheit—around 480 degrees Celsius—or greater) with commercially available catalyst, and have long residence times. The residence time is a factor of the number of reactors and the amount of catalyst involved. High severity reformers typically involve four or five reactors in series. Also, at each reactor, heating to the noted inlet temperature is required in order to produce the desired gasoline products. High severity reformers are associated with high operating costs and may result in a significant volume loss of high economic value gasoline components.

Gasoline is a blend of LSR and reformate and other gasoline components obtained from the crude, such as butane, alkylate, isopentane, methyl tertiary butyl ether, ethanol and catalytic cracker gasoline. The proper boiling point, octane number, and other gasoline specifications are met by the blend of the LSR, reformate and other gasoline components.

The benzene content of gasoline has been regulated to a low value in many nations including Canada and the United States. Refiners have chosen four methods to reduce benzene in the gasoline product in order to produce a gasoline having an octane quality sufficient to meet gasoline octane specifications. Refiners have: (1) removed benzene precursors before the naphtha reformer to preclude or reduce benzene production in the reformer; (2) hydrotreated or saturated the benzene fraction of the reformate to convert the benzene to non-aromatics; (3) developed new reformer catalysts that selectively do not react with the benzene precursors; and (4) removed benzene from the reformate or a fraction thereof by aromatics extraction. With the exception of the aromatics extraction method, each of these methods reduce the net amount of benzene available for benzene derivative production thereby increasingly moving the industry to more expensive methods to produce benzene.

Aromatics extraction is most commonly performed by solvent or extractive distillation. $C_6$ to $C_8$ aromatics are fractionated in a fractionation tower, usually into benzene and a toluene/xylenes mixture. The raffinate stream obtained after extraction of these aromatics can be blended into gasoline. Additional benzene could be produced from the toluene and xylenes recovered by fractionation using hydrodealkylation and/or toluene disproportioning processes. Producing benzene from these two processes introduces additional capital cost and volume loss of expensive feedstock.

The term "raffinate" is used throughout this application. It will be understood by the skilled reader that the composition of the raffinate will depend on the specific extraction process, and feedstock.

Alternative sources of benzene, such as pyrolysis gasoline ("pygas"), catcracker gasoline, and Coker naphtha are also available, but obtaining benzene from these sources involve high operating costs. Also, these sources, although significant in volume, are not sufficient to satisfy the world benzene market.

Another high cost process for producing benzene is the UOP/BP Cyclar process that uses propane and butane to make benzene and other aromatics. There is a world scale unit at a British Petroleum (BP) refinery in the United Kingdom. This process has the limitation of not producing a significant portion of the aromatics as benzene, thus not adequately satisfying the world benzene market.

A lower cost method to produce benzene directly in the refinery process would be beneficial.

A process and system for extraction of chemical components from a feedstock, such as petroleum, natural gas condensate or petrochemical feedstock, that maximizes high economic value streams at high volumetric yields would also be of benefit.

Attempts have been made to modify the conventional refinery process, such as by fractionating feedstock and using different reformers on each fraction, see, for example, U.S. Pat. No. 6,051,128.

SUMMARY

According to one aspect of the present invention, there is provided a method of recovering aromatics from a naphtha feedstock comprising the steps of: (a) separating from the naphtha feedstock a $C_6$ to $C_{11}$ hydrocarbon fraction; (b) recovering from the $C_6$ to $C_{11}$ hydrocarbon fraction an aromatics fraction, an aromatics precursors fraction, and a raffinate fraction in an aromatics extraction unit; (c) converting aromatics precursors in the aromatics precursors fraction to aromatics; and (d) recovering aromatics from step (c) in the aromatics extraction unit. In one embodiment, the method further comprises recycling from step (d) any unreacted aromatics precursors back to step (c).

According to another aspect of the present invention, there is provided a method of recovering aromatics from a naphtha feedstock comprising the steps of: (a) separating from the naphtha feedstock a $C_6$ to $C_{11}$ hydrocarbon fraction; (b) recovering from the $C_6$ to $C_{11}$ hydrocarbon fraction an aromatics fraction, an aromatics precursors fraction, and a raffinate fraction in an aromatics extraction unit; (c) converting aromatics precursors in the aromatics precursors fraction to aromatics in a low severity naphtha reformer; and (d) recovering aromatics from step (c) in the aromatics extraction unit. In one embodiment, the method further comprises recovering from step (d) any unreacted aromatics precursors from step (c) and returning the unreacted aromatics precursors to the low severity reformer for conversion to aromatics.

According to another aspect of the present invention, there is provided a system for recovering aromatics from crude feedstock, comprising: (a) separating from the crude feedstock in a crude distillation unit a whole range naphtha fraction; (b) separating a $C_6^+$ fraction from the whole range naphtha fraction in a naphtha splitter; (c) separating a $C_6$ to $C_{11}$ hydrocarbon fraction from the $C_6^+$ fraction; (d) recovering from the $C_6$ to $C_{11}$ hydrocarbon fraction an aromatics fraction, an aromatics precursors fraction and a raffinate fraction in an aromatics extraction unit; (e) converting aromatics precursors in the aromatics precursors fraction to aromatics in a low severity naphtha reformer; (f) recovering aromatics from step (e) in the aromatics extraction unit; and (g) optionally recovering from step (f) any unreacted aromatics precursors from step (e) and returning the unreacted aromatics precursors to the low severity reformer for conversion to aromatics.

According to another aspect of the present invention, there is provided a low severity reformer for producing $C_6$ to $C_8$ aromatics from an enriched $C_6$ to $C_8$ naphthenes feedstock, the reformer comprising one or two reactors, in parallel or in series, each having an inlet temperature of about 425 degrees Celsius, and each comprising a platinum and/or rhenium catalyst and a catalyst support system.

DETAILED DESCRIPTION

A function of a reformer is to reformulate molecules from non-aromatics (e.g., paraffins, including isoparaffins, and naphthenes) to aromatics such that gasoline octane quality specifications can be achieved. Typically, a reformer has four or five reactors in series with heaters between reactors to heat the effluent from each reactor to the reactor inlet temperature of the next reactor. The predominant reactions in the reformer are endothermic requiring this inter stage heating. Typical catalysts for use in catalytic reformers are platinum and rhenium incorporated in a catalyst support medium, each metal and support medium playing a dominant part in promoting different reactions to occur.

Reactions that occur in the reformer include: (1) isomerization of paraffins to isoparaffins; (2) hydrocracking and demethylation of paraffins (including isoparaffins); (3) dehydrocyclization of paraffins (including isoparaffins) to five membered rings; (4) isomerization of five membered rings to six membered rings; (5) dehydrogenation of six membered rings to aromatics; and (6) dealkylation, including demethylation, of aromatics. The reactions may also be described as converting naphthenes to aromatics, and converting paraffins (including isoparaffins) to either cyclic members (e.g., naphthenes and aromatics) or to smaller paraffinic members.

The reformate produced comprises aromatics including benzene, toluene and xylenes ("BTX") in various concentrations, as well as other aromatics, depending on the naphtha feed composition, typically measured as the Naphthenes+Aromatics (N+A) percent. Hydrogen gas is produced as a by-product of aromatics production in the dehydrocyclization and dehydrogenation reactions, for example. Hydrogen is consumed by hydrocracking and dealkylation (including demethylation) reactions.

In the reformer, naphthenes react very quickly and efficiently (high conversion) while paraffins react slowly and with poorer yields of aromatics and also producing light components of $C_1$-$C_4$ molecules. The naphthenic reactions, although resulting in conversion to higher density products, do not exhibit the high volume loss typical of paraffinic reactions.

Temperature and residence time in the reactors are two parameters that determine the severity of the reactions. These parameters may be controlled to produce the highest yield of aromatics. As indicated above, a conventional reformer normally comprises four or five reactors in series to attain the highest yield of aromatics in a typical operation. Most of the naphthenes are converted to aromatics in the first two reactors, while the paraffinic reactions mainly occur in the last two or three reactors.

Figure 1:
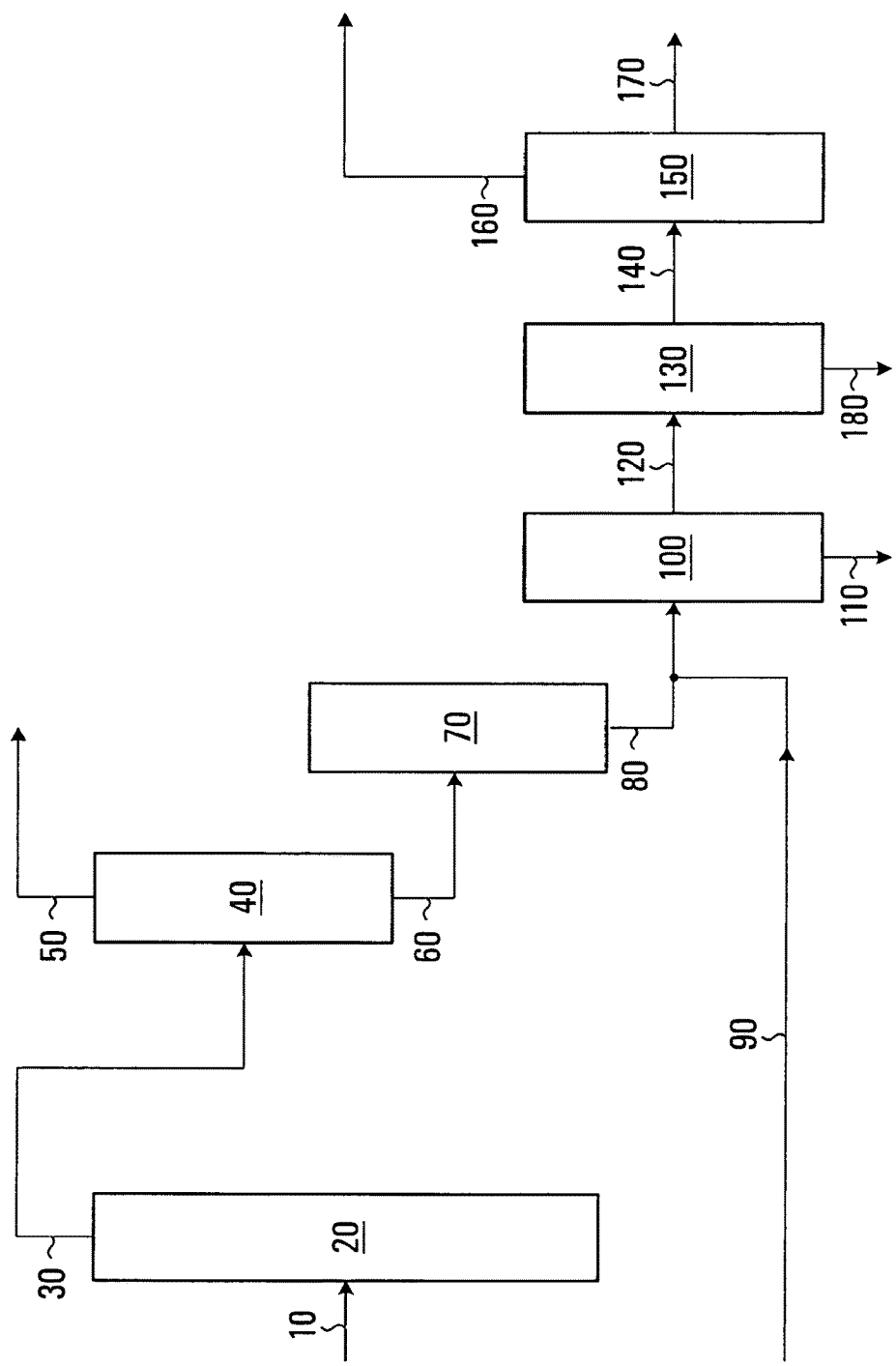
FIG. 1 illustrates a conventional refinery system for a crude feedstock.

FIG. 1 illustrates a conventional refinery process. Crude feedstock (10) is processed in a crude distillation unit (20). The whole range naphtha stream obtained (30) is processed in a naphtha splitter (40) to separate the LSR (50) from the heavy naphtha (60), which is further processed in a hydrotreater (70) to remove sulphur, and other components, such as nitrogen. The sweet naphtha stream produced (80), along with any other intermediate refinery sweet naphtha feed streams (90) that may be added, are treated in high severity naphtha reformer (100) to obtain a reformate (110). A $C_6$ to $C_8$ reformate stream (120) can also be recovered and further processed in an aromatics extraction unit (130). Aromatics (140) may be further fractionated in a selective fractionation unit (150), usually into a benzene (160) fraction, and a toluene/xylenes mixture (170). The raffinate stream (180) obtained following aromatics extraction can be blended into gasoline.

As described above, high severity naphtha reformers used in conventional practice involve high temperatures and long residence times to obtain BTX and other aromatics meeting the gasoline octane specification. High severity reforming results in a significant volume loss across the reactors of the naphtha reformer and may crack some benzene precursors to lower value products. Also, and as described above, the effluent from each reactor stage needs to be reheated for the next stage to produce sufficient aromatics. Reforming the aromatics achieves no benefit, as the aromatics are the desired product, and increases capital and operating costs, in part because of the volume of material being heated at each stage.

In the present invention, naturally occurring aromatics are recovered from a naphtha stream following processing in a naphtha splitter and prior to naphtha reforming. $C_6$ to $C_{11}$ aromatics and aromatic precursors may be recovered as concentrated streams. Benzene and/or other aromatics, including toluene and xylenes, may then be recovered directly without reforming. Benzene precursors and/or other aromatics precursors may then be sent to a low severity high yield reformer for conversion into benzene and/or other aromatics. In another embodiment, instead of a low severity reformer, another unit (such as a commercially available dehydrogenation unit or a high severity reformer) that converts naphthenes to aromatics may be used.

A low severity reformer targets the naphthenic reactions. Compared to a high severity reformer, a low severity reformer is operated at shorter residence times and lower temperatures. A low severity reformer may comprise only one or two reactors compared to the four or five of a conventional naphtha reformer. Also, each reactor of the low severity reformer may be operated at an inlet temperature of about 800 degrees Fahrenheit (about 425 degrees Celsius) or greater. The temperature of the low severity reformer will depend, in part, on the choice of catalyst and catalyst support, as would be understood by a person skilled in the art. The lower temperature and shorter residence time of a low severity reformer may reduce the paraffinic reactions that may occur in a high severity reformer.

The catalyst used in the low severity reformer may be selected to target the naphthenic reactions as opposed to the paraffinic reactions. Suitable catalysts or catalyst systems would be known to the person skilled in the art, and include, for example, commercially available platinum and/or rhenium catalysts on a zeolite support.

The pressure of the low severity reformer may also be selected to optimize aromatics production, usually 200 pounds per square inch gauge (PSIG) or lower.

If more than one reactor is used in the low severity reformer, the reactors may be in series or parallel. Using reactors in series may further promote paraffinic reactions. To further reduce the possibility of paraffinic reactions, the reactors may therefore be used in parallel.

Figure 2:
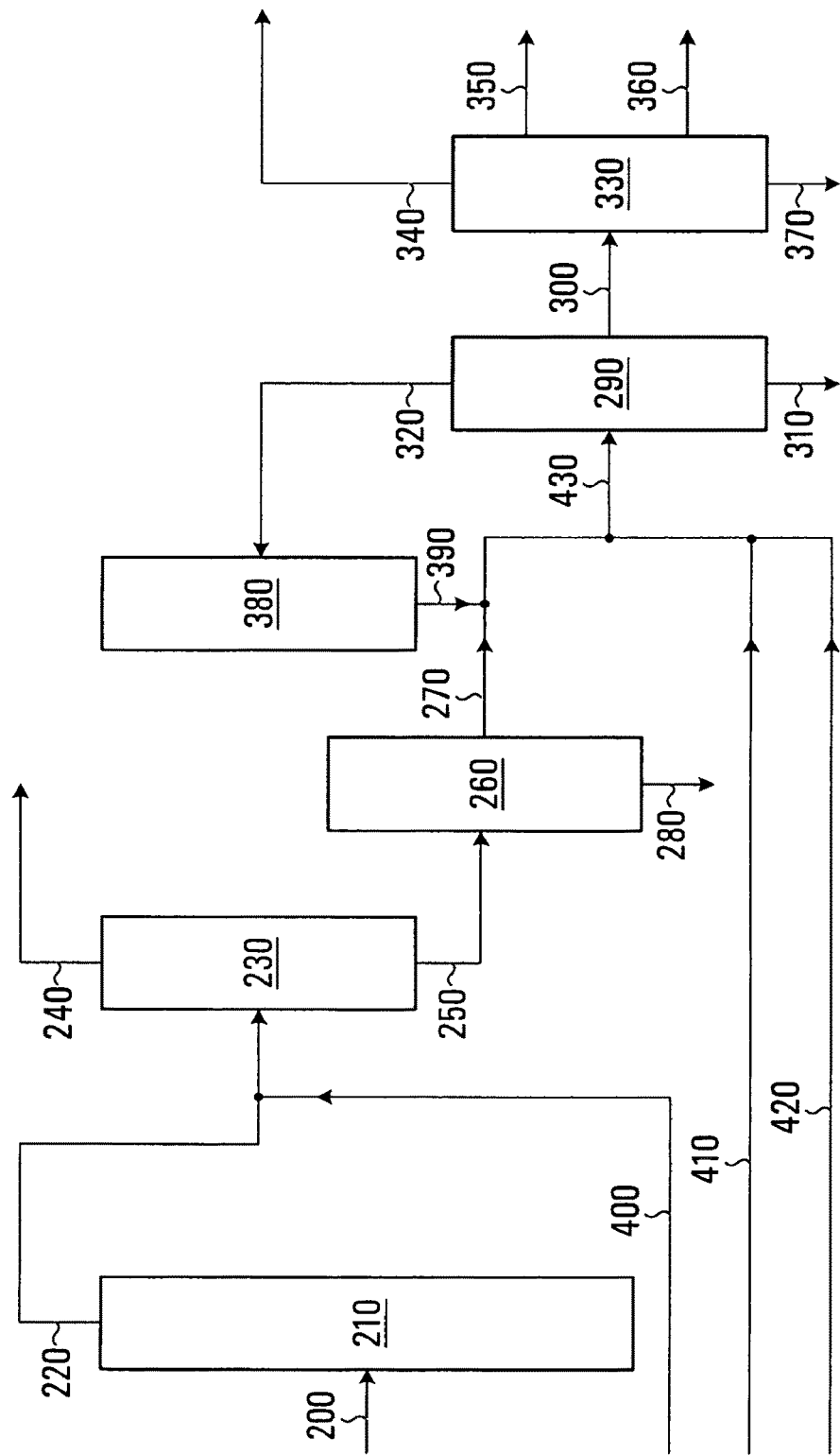
FIG. 2 illustrates a refinery system according to an embodiment of the present invention.

FIG. 2 illustrates one embodiment of the present invention. According to this embodiment, a crude feedstock (200) is treated in a crude distillation unit (210) to obtain a whole range naphtha stream (220). The whole range naphtha stream (220) is further processed in a naphtha splitter (230).

In the naphtha splitter (230), a LSR fraction comprising $C_1$ to $C_6$ hydrocarbons (240) may be separated from a heavy naphtha fraction comprising $C_6^+$ hydrocarbons (250). The $C_1$ to $C_6$ fraction comprises mainly linear or branched hydrocarbons. This fraction may be further processed in, for example, a debutanizer (not shown) to optionally recover: fuel gas, which may be used, for example, to fuel the process of the invention; butane; and a fraction comprising $C_5$ and $C_6$ hydrocarbons that may be routed to the gasoline pool. Naphthenes and aromatics are concentrated in the heavy $C_6^+$ fraction. According to an invention embodiment, the naphtha splitter (230) may comprise a commercially available deisohexanizer or a commercially available demethylcyclopentanizer, or a tower designed for both services, which may be used to recover methylcyclopentane (MCP). Use of the demethylcyclopentanizer recovers MCP, as part of the overheads, that may be routed to the gasoline pool, and the deisohexanizer may be used to route the MCP, as part of the bottoms, and ultimately to the low severity reformer or other unit for converting aromatics precursors to aromatics.

The $C_6^+$ fraction (250) can be separated in a hydrotreater unit (260) into a $C_6$ to $C_{11}$ fraction (270) and a $C_{12}^+$ fraction (280) and sour fuel gas (not shown). The hydrotreater unit (260) is used to remove sulphur (i.e., hydrodesulfurization), and possibly nitrogen (i.e., hydrodenitrogenation), and may comprise a stabilizer plus a fractionation tower or the stabilizer may be a combination stabilizer/fractionation unit. There are a number of commercially available hydrotreating units that may be used in this step. The hydrotreater unit (260) may also convert any olefins to paraffins, and the $C_6$ to $C_8$ paraffins may then be recovered (not shown) and, for example, used as feedstock for a steam cracker. The CrystaSulf™ process of CrystaTech or a known sour gas treatment process may also be used to remove sulphur from the sour fuel gas stream, which may then be used, for example, as fuel. The $C_{12}^+$ fraction (280) recovered may be used in the production of distillate, diesel or jet fuel, for example.

The $C_6$ to $C_{11}$ fraction (270) may then be subjected to aromatics extraction in an aromatics extraction unit (290). The composition of $C_6$'s in the $C_6$ to $C_{11}$ fraction (270) will depend in part on whether or not the naphtha splitter (230) comprises a deisohexanizer or a demethylcyclopentanizer. If it does not include either unit (or any other fractionation unit), the whole range of $C_6$ hydrocarbons will be present in the $C_6$ to $C_{11}$ fraction (270). If a deisohexanizer is used, the $C_6$'s include benzene, cylcohexane and MCP in the $C_6$ to $C_{11}$ fraction (270), and if a demethycyclopentanizer is used, the $C_6$'s include benzene and cyclohexane in the $C_6$ to $C_{11}$ fraction (270).

Any aromatics extraction unit (290) could be used, including, for example, an aromatics extractive distillation unit commercially available from GTC Technology, such as the GTC GT-BTX™ unit. The aromatics extraction unit (290) is used to produce a stream of $C_6$ to $C_{11}$ aromatics (300), and a raffinate (310, 320) comprising $C_6$ to $C_{11}$ paraffins, isoparaffins, and naphthenes.

The aromatics fraction (300) may be routed to a selective distillation unit (330) to selectively recover aromatics (340, 350, 360). For example, benzene could be selectively recovered in a benzene distillation unit; or, in another embodiment, a xylenes distillation unit could be used to recover a benzene fraction, a toluene fraction, and a xylenes fraction. The fraction (370) comprising any aromatics remaining after selective distillation could be routed to the gasoline pool, for example.

Where solvent is added in the aromatics extraction process, the aromatics fraction (300) recovered may first be routed to a solvent stripper (not shown) to recover the solvent before the aromatics fraction is further fractionated. Solvent recovered may be recycled to the aromatics extraction unit (290).

According to another embodiment of the invention, benzene and xylenes are selectively concentrated prior to aromatics extraction. A stream of $C_6$'s as overheads and $C_8$'s as bottoms could be obtained, and these fractions could be combined and routed to the aromatics extraction unit to recover benzene and xylenes. The mid-stream $C_7$'s could then be combined with the raffinate from the aromatics extraction unit.

In the aromatics extraction process, aromatics precursors (320) are concentrated and separated from the remaining components of the raffinate, which remainder (310) may be routed to a gasoline pool for use in making gasoline, and/or which may be further treated to remove $C_6$ to $C_8$ paraffins. The $C_6$ to $C_8$ paraffins may be used, for example, as feedstock for a steam cracker.

Aromatic precursors may be routed to a low severity reformer (380), or a dehydrogenation or other unit, as discussed above, which has the function of converting aromatics precursors to aromatics. The reformate/conversion product (390) comprising aromatics and any unreacted aromatic precursors may then be routed to the aromatics extraction unit (290) for further processing.

The aromatics precursors (320) recovered from the aromatics extraction unit (290) may also be concentrated into selected fractions (not shown). In this manner, selected fractions could be routed to the low severity reformer (or other unit for converting aromatics precursors to aromatics), with non-selected precursors forming part of the raffinate (310), which could be sent to, for example, a conventional reformer. Also, the aromatics precursors fraction will normally include other hydrocarbons in addition to aromatics precursors, such as paraffins, which could also be selectively recovered. In an exemplary embodiment, normal paraffins are recovered, and, for instance, routed to a steam cracker, or routed to distillate blending. In one embodiment it is $C_6$ to $C_8$ normal paraffins that are so recovered.

$C_6$ and $C_7$ hydrocarbons have a boiling point of up to about 220 degrees Fahrenheit (about 104 degrees Celsius). $C_8$ hydrocarbons have a boiling range of about 220 to about 265 degrees Fahrenheit (about 104 to about 129 degrees Celsius). The $C_9$ to $C_{11}$ hydrocarbons have a boiling point of about 265 degrees Fahrenheit (about 129 degrees Celsius) or greater. These fractions may therefore be separated by distillation, and then further separated into their paraffinic and naphthenic components by way of a further distillation.

For instance, a $C_6$ fraction could be separated using a commercially available fractionation unit (e.g., a dehexanizer) into a hexanes feedstock for use in, for instance, a steam cracker, and a fraction high in $C_6$ naphthenes for treatment in the low severity reformer (or other unit). Similarly, $C_7$ and $C_8$ fractions could be separated in commercially available fractionation units (e.g., a deheptanizer and deoctanizer, respectively) into heptane and $C_7$ naphthenes and into octane and $C_8$ naphthenes, respectively. The heptanes and octanes may be sent to a steam cracker, for example, and the $C_7$ and $C_8$ naphthenes may then be sent to the low severity reformer (or other unit). In another invention embodiment, instead of using a distillation process, a molecular sieve or sorbent may be used. Examples include adsorbents available from UOP, and, UOP's Sorbex™ or MaxEne™ processes. These processes utilize molecular adsorptive solvents or solids to selectively remove paraffins from hydrocarbons thereby separating into a paraffin and non-paraffin stream (for example, naphthenes). By using a distillation or other separation process, $C_6$ to $C_8$ naphthenes may be selectively routed to the low severity reformer (380), or another unit for converting aromatics precursors to aromatics. By using a distillation or other separation process, the concentration of aromatic precursors in stream (320) may be increased to, for example, about 75-80% v/v with the remaining components being mainly isoparaffins.

It may be necessary for the aromatics precursors stream (320) to be run through a sulphur guard bed (not shown) to remove traces of sulphur before reforming in the low severity reformer (380), or before treatment in another unit for converting aromatics precursors to aromatics. The precursor stream (320) may also be recycled (not shown) to the hydrotreater unit (260) to remove sulphur and/or nitrogen and/or saturate olefins.

The low severity reformer (or other unit) can be monitored for increasing concentrations of non-aromatics precursors. If increasing, a stream of the non-aromatics precursors (not shown) could be separated from the aromatics precursors stream routed to the low severity reformer (or other unit). The non-aromatics precursors stream may then be, for instance, routed to the gasoline pool, used as feedstock for a steam cracker, or subjected to another distillation or extraction process to remove paraffins and isoparaffins for the gasoline pool or as a feedstock for a steam cracker, etc.

The reformate/conversion product (390) may be routed to the aromatics extraction unit (290) for extraction of aromatics. Any unreacted aromatic precursors (320) could be returned for further processing to the low severity reformer (380) or other unit used for converting aromatics precursors to aromatics. High naphthenic concentrations may therefore be maintained in the low severity reformer or other unit. Also, by concentrating the feedstock in naphthenic content in this manner, the possibility of paraffinic reactions may further be reduced.

One or more additional feed streams (400) may optionally be added as supplemental feed to the naphtha splitter (230), and/or one or more additional feed streams (410, 420) may also be added and directed to the aromatics extraction unit as a combined stream (430) with the $C_6$ to $C_{11}$ fraction (270) and/or the reformate/conversion product (390). If the additional feed (410, 420) is first mixed with the reformate/conversion product (390), the mixed stream may optionally be split to concentrate selected aromatics and/or aromatics precursors. By splitting the stream a stream concentrated in single double bond olefins and aromatics suitable for gasoline blending may also be obtained.

The one or more additional feed streams (400, 410, 420) may be chosen from feedstocks having a high $C_4$ to $C_8$ content, with the majority of components in the $C_5$ to $C_6$ ranges. For example, streams with a high proportion of benzene precursors, such as methylcyclopentane and cyclohexanes, and toluene and xylenes precursors; feed streams of olefinic material having high concentrations of aromatics and aromatic precursors; and feed streams having a high proportion of aromatics may be chosen. A stream low in sulphur, nitrogen and olefins may be routed directly to the naphtha splitter (230) or aromatics extraction unit (290); otherwise, the stream may first be subjected to, for example, a hydrotreating step, solvent extraction, caustic soda treatment, etc. This initial step of concentrating the feedstock (400, 410, 420) may also increase the volume of aromatics produced.

The one or more additional feed streams (400, 410, 420) may, for example, comprise one or more of a condensate (e.g., a non-refinery intermediate stream) comprising aromatics and/or aromatic precursors; natural gasoline comprising aromatics and/or aromatic precursors; and a refinery reformate low in sulphur components but comprising aromatics and/or aromatic precursors. An example of an additional feed is pygas. The pygas may be subjected to an initial liquid phase hydrogenation prior to aromatics extraction, to remove sulfur and to saturate any olefins containing two or more double bonds or triple bonds to single double bond olefins. A fraction that is concentrated in single double bond olefins can then be recovered by, for example, distillation and sent to the gasoline pool, for example. A $C_6$ to $C_8$ aromatics fraction can also be obtained by, for example, distillation, and which fraction may then be routed to the aromatics extraction unit (290). Other additional feedstreams would be known to a person skilled in the art.

The skilled person will understand that where reference is made to, for example, a feedstream "low" in sulfur or other components, the concentration of the components in the feedstream is sufficiently low to meet product specifications.

Benzene, toluene and xylenes precursors may be simultaneously processed in the low severity reformer (380), or other unit for converting aromatics precursors to aromatics. BTX may then be recovered in the aromatics extraction unit (290), or benzene, toluene and xylenes selectively recovered in a selective distillation unit (330), as described above.

The process of the invention may also be optimized to selectively produce benzene, toluene or xylenes, or a combination thereof, such as by optimizing severity of the low severity reformer and/or by optimizing feedstock variables of the low severity reformer or other unit for converting aromatics precursors to aromatics. For instance, the feedstock may be varied by selectively concentrating benzene, toluene and/or xylenes precursors from the aromatics extraction unit by distillation or another extraction process using, for example, a molecular sieve or sorbant, as discussed above. Also, the constitution of the feedstock may be altered by adding condensate or other refinery or petrochemical streams high in benzene, toluene and/or xylenes to the aromatics extraction unit, also as discussed above.

The hydrogen produced (not shown) as a by-product of the reforming step may be recovered and used in the hydrotreatment step, and/or may be recovered as a high economic value stream, such as hydrogen by using a known hydrogen purification process.

The sulphur obtained from the various desulphurizing steps described herein may be collected and may be combined. Sulphur obtained may be useful for the production of agricultural products, for example.

Also, the skilled person will appreciate that other hydrocarbon streams may be selectively recovered at different stages of the process described above, including, for example, liquefied petroleum gas (LPG), jet fuel, diesel, vacuum gas oil (VGO), and other product streams not specifically mentioned above using methods known to one skilled in the art. Product streams may be subjected to further processing as would be apparent to the skilled person.

A low severity reformer for use in the present invention may be obtained using known reformer technology with reactors and operating parameters adjusted as described above as would be understood by a person skilled in the art.

The process of the invention does not have to be practiced in a refinery setting. It may be practiced as a "stand alone" process to produce aromatics such as benzene, xylenes and/or toluene, and/or to concentrate aromatics precursors of, for example, benzene, toluene and/or xylenes. The stand alone process may then be used to feed an existing refinery. The naphtha splitter, hydrotreater unit, aromatics extraction unit, and low severity reformer or other unit for converting aromatics precursors to aromatics could constitute an "off site" plant.

According to another embodiment of the invention, an initial desulphurizing step (not shown) may also be used. In one invention embodiment, the whole range naphtha (220) from the crude distillation unit (210) is first subjected to a conventional caustic treating addition or the Minalk™ process to remove mercaptans from the light naphtha prior to routing to the naphtha splitter (230). The sweetened LSR could then be recovered as overheads from the naphtha splitter (230) to be routed to gasoline blending, for example, as described above. The additional desulphurizing step may optimize the hydrotreater unit (260), such as by allowing a smaller unit, resulting in a potential cost savings.

In another invention embodiment, the initial desulphurizing step is the only desulphurizing step employed in the process of the invention. In this embodiment the whole range naphtha (220) is subjected to a desulphurizing (e.g., hydrotreating) before routing to the naphtha splitter (230). The sweetened LSR is then recovered, and the heavy naphtha then fractionated (e.g., by distillation) into a $C_6$ to $C_{11}$ fraction (270), which is then further treated in the manner described above.

In a conventional refinery configuration, the volume loss across a high severity reformer processing heavy naphtha is about 20 to 35% calculated based on N+2A (i.e., the concentration of Naphthenes plus twice the concentration of Aromatics in the feedstock). Volume losses by using a process of the present invention across the low severity reformer are projected to be about 10%. The overall volume loss of about 5% is therefore expected to be lower than typical losses of the order of 15% to 25% using conventional process technology.

By using a process according to the present invention a hydrogen production surplus may also be obtained that is greater than in a conventional refinery scheme. In a conventional reformer the hydrogen stream volumetric yield is about 0.8 to 1.0 moles per mole of naphtha feed, and depends on the N+2A quality of the feedstock. By using a low severity reformer according to the present invention 2.5 to 3.5 moles hydrogen per mole of naphtha feed may be obtained, depending on the quality of the feedstock.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The citation of any publication, patent or patent application is for its disclosure prior to the filing date and should not be construed as an admission that the present invention is not entitled to antedate such publication, patent or patent application by virtue of prior invention.

It must be noted that as used in the specification and the appended claims, the singular forms of "a", "and" "the" include plural reference unless the context clearly indicates otherwise.

Unless defined otherwise all technical and scientific terms used herein have the same meaning as commonly understood to one of ordinary skill and the art to which this invention belongs.

What is claimed is:

1. A system for recovering aromatics from a naphtha feedstock, comprising:
   (a) a naphtha splitter for separating a C6+ fraction from the naphtha feedstock;
   (b) a hydrotreater unit to desulphurize and separate a C6 to C11 hydrocarbon fraction from the C6+ fraction;
   (c) an aromatics extraction distillation unit for recovering from the C6 to C11 hydrocarbon fraction an aromatics fraction, an aromatics precursors fraction and a raffinate fraction;
   (d) a dehydrogenation unit or a reformer for converting the aromatics precursors in the aromatics precursors fraction to aromatics; and
   wherein the naphtha splitter, the hydrotreater unit, and the aromatic extraction distillation unit, are operatively connected such that the C6+ fraction and the C0 to C11 hydrocarbon fraction are not subjected to a reformer or a dehydrogenation unit prior to the recovery of the aromatics fraction, the aromatics precursors fraction and the raffinate fraction.

2. A system for recovering aromatics from a naphtha feedstock, comprising:
   (a) a naphtha splitter for separating a C6+ fraction from the naphtha feedstock;
   (b) a hydrotreater unit or a distillation unit for separating a C6 to C11 hydrocarbon fraction from the C6+ fraction;
   (c) an aromatics extraction distillation unit for recovering from the C6 to C11 hydrocarbon fraction an aromatics fraction, an aromatics precursors fraction and a raffinate fraction;
   (d) a dehydrogenation unit or a reformer for converting the aromatics precursors in the aromatics precursors fraction to aromatics; and
   wherein the hydrotreater unit or distillation unit for separating the C6 to C11 hydrocarbon fraction from the C6+ fraction, and the aromatic extraction distillation unit, are operatively connected such that the C6 to C11 hydrocarbon fraction is not subjected to a reformer or a dehydrogenation unit prior to the recovery of the aromatics fraction, the aromatics precursors fraction and the raffinate fraction,
   the system further comprising (e) a desulphurizing unit for removing sulfur from the naphtha feedstock prior to the separating of the C6+ fraction.

3. The system according to claim 2, wherein the desulphurizing unit is a caustic treating system.

4. The system according to claim 2, wherein component (b) is a distillation unit and the desulphurizing unit is a hydrotreater unit.

5. The system according to claim 1, which further comprises a fractional distillation unit for removal of paraffins from the aromatics precursor fraction, and for concentration of naphthenes in the aromatics precursors fraction.

6. The system according to claim 5 wherein the fractional distillation unit is for removal of C6, C7, or C8 paraffins, or a combination thereof.

7. The system according to claim 5 wherein the fractional distillation unit is for concentration of C6, C7, or C8 naphthenes, or a combination thereof, in the aromatics precursors fraction.

8. The system according to claim 1, which further comprises a molecular sieve or sorbent for removal of paraffins from the aromatics precursor fraction, and for concentration of naphthenes in the aromatics precursors fraction.

9. The system according to claim 8, wherein the molecular sieve or sorbent is for removal of C6, C7, or C8 paraffins, or a combination thereof, from the aromatics precursor fraction.

10. The system according to claim 8, wherein the molecular sieve or sorbent is for concentration of C6, C7, or C8 naphthenes, or a combination thereof, in the aromatics precursors fraction.

11. The system according to claim 1, wherein a splitter comprises a deisohexanizer or a demethylcyclopentanizer.

12. The system according to claim 1, wherein component (d) is a dehydrogenation unit.

13. The system according to claim 1, wherein component (d) is a conventional reformer.

14. The system according to claim 1, wherein component (d) is a low severity naphtha reformer.

* * * * *